(12) United States Patent
Metz-Stavenhagen

(10) Patent No.: US 9,713,513 B2
(45) Date of Patent: Jul. 25, 2017

(54) DENTAL IMPLANT

(76) Inventor: Peter Metz-Stavenhagen, Bad Wildungen (DE)

( * ) Notice: Subject to any disclaimer, the term of this patent is extended or adjusted under 35 U.S.C. 154(b) by 0 days.

(21) Appl. No.: 12/755,673

(22) Filed: Apr. 7, 2010

(65) Prior Publication Data

US 2010/0261142 A1 Oct. 14, 2010

(30) Foreign Application Priority Data

Apr. 8, 2009 (DE) .................. 10 2009 016 920

(51) Int. Cl.
*A61C 8/00* (2006.01)

(52) U.S. Cl.
CPC .......... *A61C 8/0022* (2013.01); *A61C 8/0039* (2013.01)

(58) Field of Classification Search
CPC ... A61C 8/0022; A61C 8/0037; A61C 8/0018; A61C 8/0024; A61C 8/0039
USPC ........... 433/173, 174, 172, 175, 176, 201.1, 433/202.1, 215, 220, 221
See application file for complete search history.

(56) References Cited

U.S. PATENT DOCUMENTS

| | | | | |
|---|---|---|---|---|
| 3,732,621 A * | 5/1973 | Bostrom | ................. | 433/174 |
| 4,790,753 A * | 12/1988 | Fradera | ................. | 433/174 |
| 4,793,808 A * | 12/1988 | Kirsch | ................. | 433/173 |
| 4,863,383 A * | 9/1989 | Grafelmann | ................. | 433/174 |
| 4,960,381 A * | 10/1990 | Niznick | ................. | 433/174 |
| 5,071,351 A * | 12/1991 | Green et al. | ................. | 433/173 |
| 5,180,303 A * | 1/1993 | Hornburg et al. | ................. | 433/173 |
| 5,269,686 A * | 12/1993 | James | ................. | 433/174 |
| 5,433,606 A * | 7/1995 | Niznick et al. | ................. | 433/173 |
| 5,871,356 A * | 2/1999 | Guedj | ................. | 433/174 |
| 5,890,902 A | 4/1999 | Sapian | | |
| 5,954,504 A * | 9/1999 | Misch et al. | ................. | 433/174 |
| 6,019,760 A * | 2/2000 | Metz-Stavenhagen et al. | ................. | 606/270 |
| 6,227,859 B1* | 5/2001 | Sutter | ................. | 433/173 |
| 6,287,117 B1* | 9/2001 | Niznick | ................. | 433/173 |
| 7,632,280 B2* | 12/2009 | Hochman | ................. | 606/94 |
| 2005/0064368 A1 | 3/2005 | Kitamura et al. | | |
| 2005/0164146 A1* | 7/2005 | Cantor | ................. | 433/173 |

(Continued)

FOREIGN PATENT DOCUMENTS

| | | |
|---|---|---|
| DE | 3735378.0 | 10/1987 |
| DE | 3735378 | 7/1988 |

(Continued)

OTHER PUBLICATIONS

"Communication about Intention to Grant a European Patent," machine translation of communication issued by the European Patent Office in connection with European Patent No. EP2238943, on Apr. 29, 2013, translation provided via [https://translate.googleusercontent.com/translate_f], 11 pages.

(Continued)

*Primary Examiner* — Matthew Nelson
(74) *Attorney, Agent, or Firm* — Hanley, Flight & Zimmerman, LLC

(57) ABSTRACT

The subject matter of the disclosure is, in one example, a dental implant having a corpus, an external thread attached on the endosteal area of the corpus, and a post accommodation formed in the inside of the corpus. Providing a dental implant that can be anchored well in the jaw is achieved by forming a recess on the endosteal end of the corpus oriented coaxially to the longitudinal axis of the corpus.

22 Claims, 5 Drawing Sheets

(56) References Cited

U.S. PATENT DOCUMENTS

2007/0162024 A1* 7/2007 Siemonsmeier ............... 606/72
2007/0292820 A1 12/2007 Canter
2008/0213729 A1* 9/2008 Hochman ..................... 433/215

FOREIGN PATENT DOCUMENTS

| DE | 102006013456 A1 | 3/2006 | | |
|---|---|---|---|---|
| DE | 102006013456 | 9/2007 | | |
| EP | 784967 A2 * | 7/1997 | ............... | A61F 2/44 |
| GB | 2199626 A * | 7/1988 | ............... | A61C 8/00 |
| WO | 2005/065571 A1 | 12/2004 | | |
| WO | WO 2005065571 A1 * | 7/2005 | ............... | A61C 8/00 |
| WO | WO 2007073743 A1 * | 7/2007 | ............. | A61B 17/86 |

OTHER PUBLICATIONS

"Extended European Search Report and Search Opinion," machine translation of the extended European search report and opinion issued by the European Patent Office in connection with European Patent No. EP2238943, on Apr. 29, 2013, translation provided via [https://translate.googleusercontent.com/translate_f], 9 pages.

"Decision to Grant a European Patent," machine translation of communication issued by the European Patent Office in connection with European Patent No. EP2238943, on Aug. 16, 2013, translation provided via https://translate.googleusercontent.com/translate_f, 3 pages.

* cited by examiner

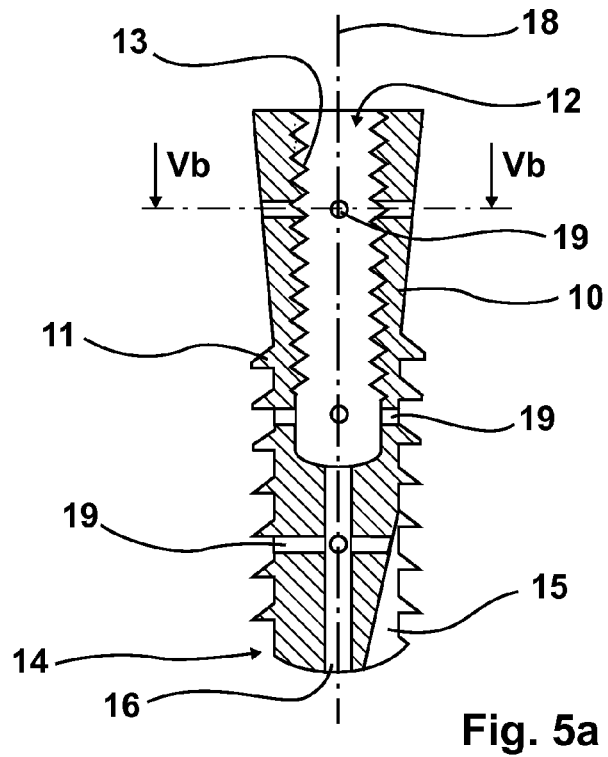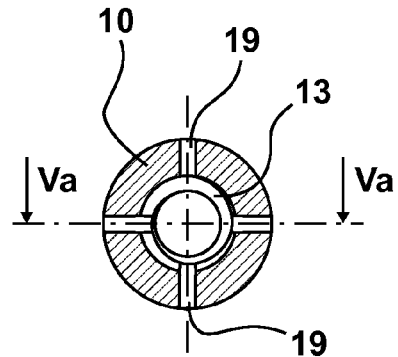
Fig. 5a       Fig. 5b
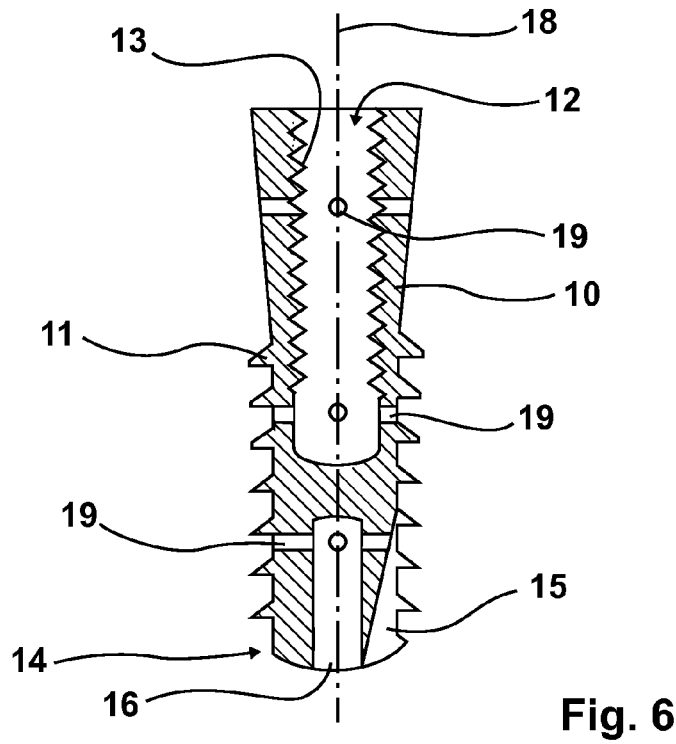
Fig. 6

DENTAL IMPLANT

CROSS-REFERENCE TO RELATED APPLICATIONS

This patent claims Priority from German Application No. DE 10 2009 016 920.2-43 filed on 8 Apr. 2009.

BACKGROUND

1. Technical Field

The present disclosure relates to a dental implant and, more particularly to a dental implant having a corpus, an external thread attached on the endosteal area of the corpus and a post accommodation formed in the inside of the corpus, wherein a recess is formed on the endosteal end of the corpus coaxially to the longitudinal axis of the corpus.

2. Description of the Prior Art

From WO 2005/065571 A 1 a multi-piece dental implant with an external thread is known on the coronal end of which an internal post accommodation is formed. An arched post, if required, can be inserted into this post accommodation onto which a dental prosthesis can be attached. On the outside of said dental implant longitudinal flattenings are defined, in order to prevent twisting of the implanted dental implant, and hence achieve a good and permanent anchoring of the dental implant in the jaw.

From DE 10 2006 013 456 A 1 a single-piece dental implant with an endosteal and a coronal area is known which is provided with an external thread. On the endosteal area at least a longitudinal, concave recess is formed in order to make twisting of the dental implant more difficult, as soon as bone substance has formed in the cavity thus developed, in order to achieve consequently a good and permanent anchoring of dental implant in the jaw.

It has turned out, however, that such flattenings or concave recesses have only a minor impact on good and permanent anchoring of the dental implant.

From WO 2007/073743 A1 a single-piece dental implant is known the interior of which features a through hole. On the endosteal end of the corpus, said through hole at first has a cylindrical shape with subsequent conical and cylindrical portions. A plurality of perforations are provided on the circumference of the dental implant which are connected with the through hole.

From DE 37 35 378 C2 a metal implant with an anchoring device is known on the endosteal end of which a blind hole is provided. Transversely to the blind hole two radially oriented openings are provided connected with the blind hole. Said blind hole is of cylindrical shape.

From U.S. Pat. No. 5,871,356 A dental implant is known on the endosteal end of which a horizontal opening is provided followed by radially projecting openings.

For all last mentioned dental implants it is necessary to pre-drill a corresponding hole in the jaw before the dental implant is inserted. It is known that this pre-drilling cannot always be made 100% precise. It may happen that the drill is applied obliquely or that weaknesses or defects occur due to a jaw subject to osteoporosis.

BRIEF DESCRIPTION OF THE DRAWINGS

FIG. 5a is a sectional view of a fifth embodiment of a dental implant described herein cut along line Va-Va in FIG. 5b.

FIG. 5b is a sectional plan view of the dental implant according to FIG. 5a, cut along line Vb-Vb in FIG. 5a.

FIG. 6 is a sectional view of a sixth embodiment of a dental implant described herein.

DETAILED DESCRIPTION

Figure 1:
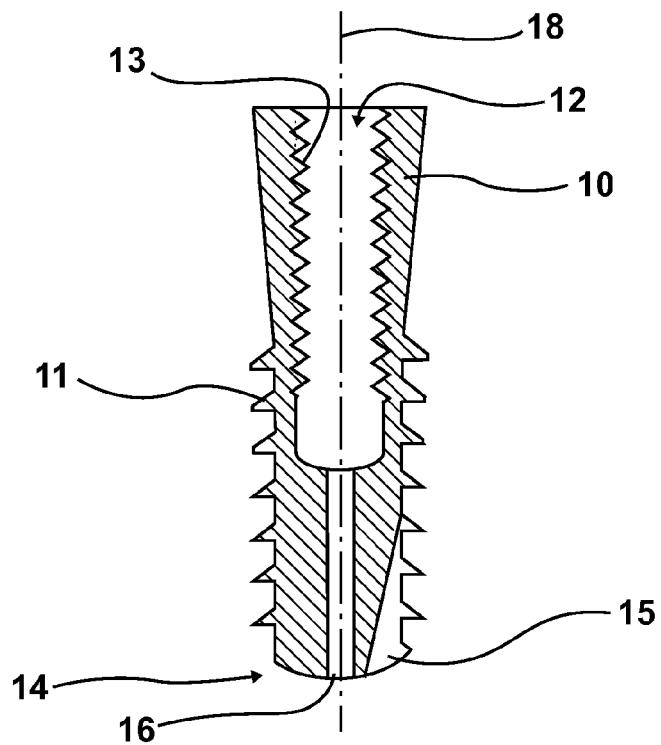
FIG. 1 is a sectional view of a first embodiment of a dental implant described herein.
Figure 2:
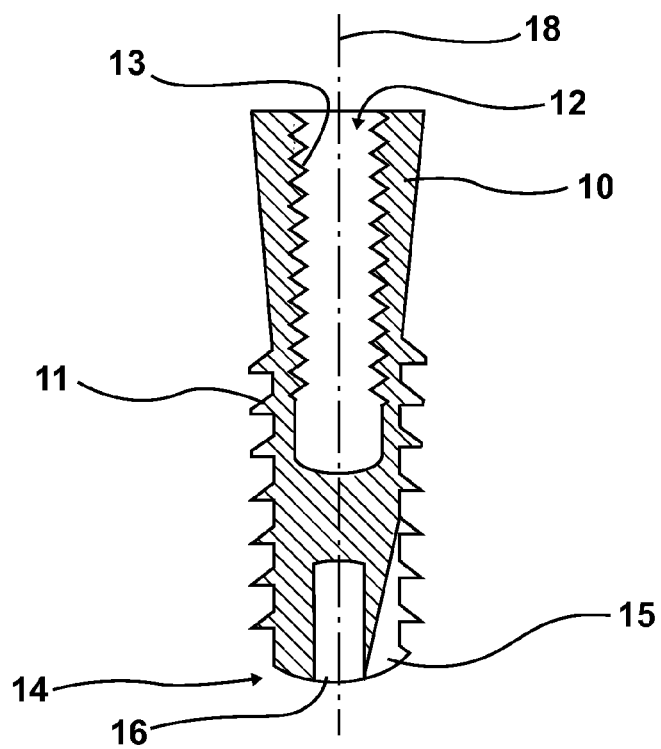
FIG. 2 is a sectional view of a second embodiment of a dental implant described herein.
Figure 3:
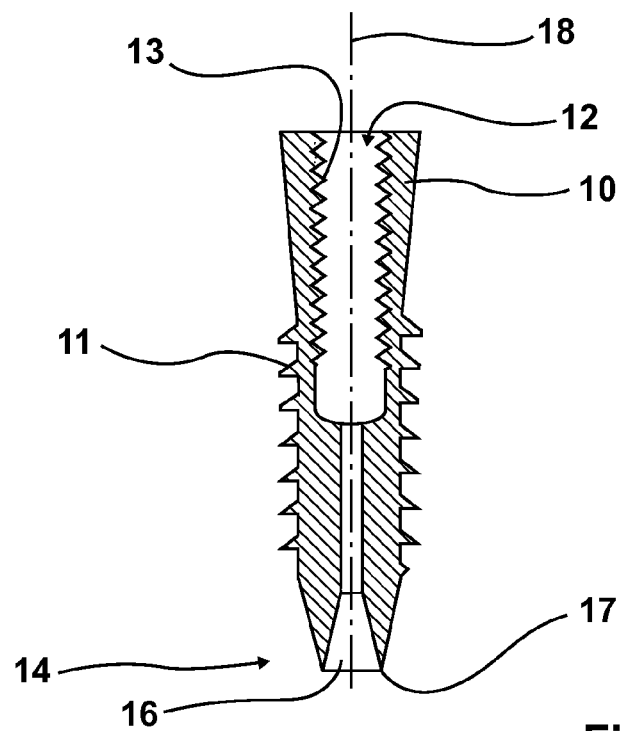
FIG. 3 is a sectional view of a third embodiment of a dental implant described herein.
Figure 4:
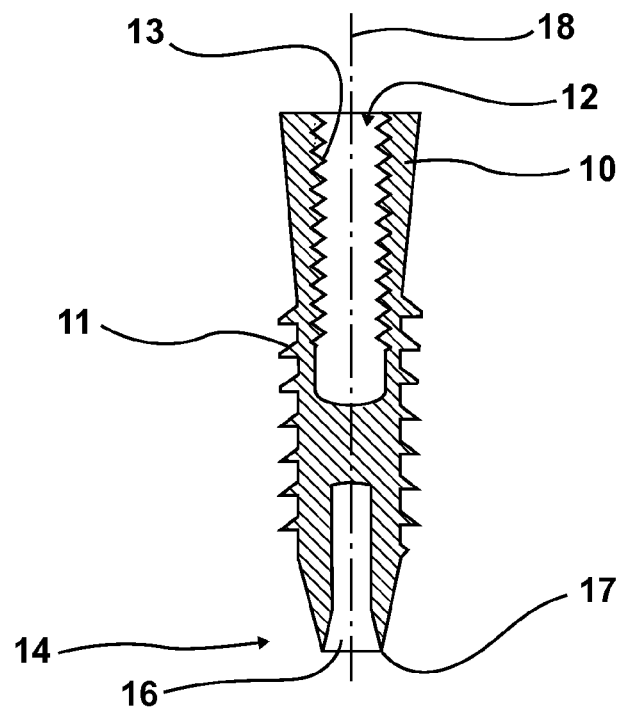
FIG. 4 is a sectional view of a fourth embodiment of a dental implant described herein.
Figure 7:
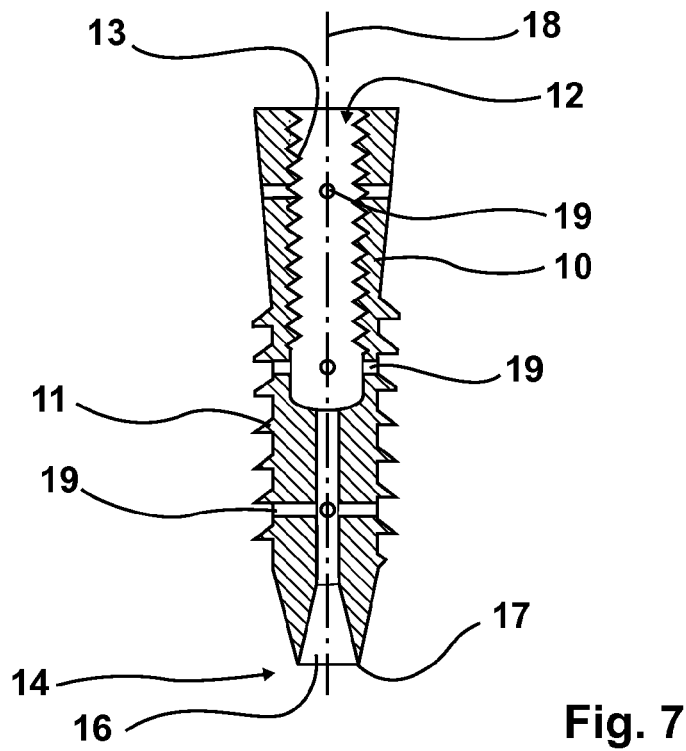
FIG. 7 is a sectional view of a seventh embodiment of a dental implant described herein.
Figure 8:
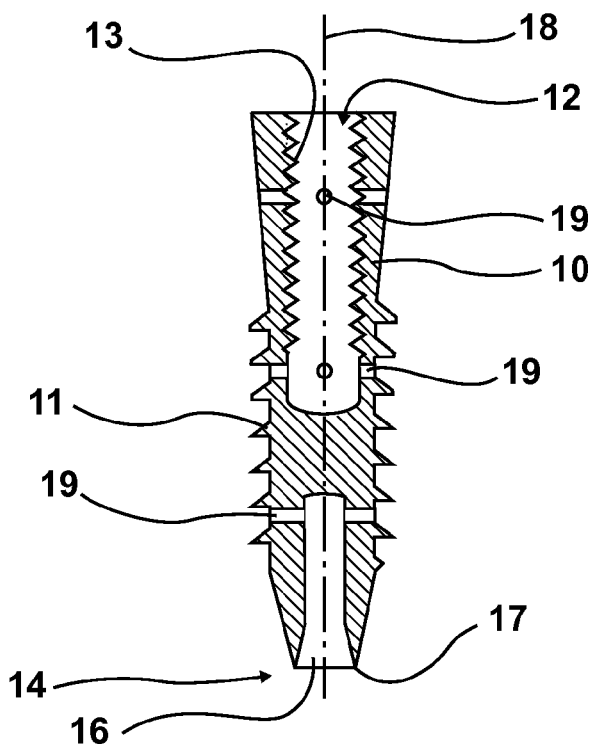
FIG. 8 is a sectional view of an eighth embodiment of a dental implant described herein.

In FIGS. 1 to 8 eight different examples of a multi-piece dental implant are shown with only the implant portion to be inserted into the jaw being illustrated here for reasons of clarity. This multi-piece dental implant comprises a corpus 10 with an external thread 11 and a post accommodation 12 formed on the coronal end of the corpus 10. The post accommodation 12 comprises an internal thread 13 for receiving a post provided with an external thread not shown here in detail.

On the endosteal end 14 of the corpus 10 an incision 15 is formed facilitating the screwing in of the dental implant into the jaw. On the endosteal end 14 moreover a recess 16 is provided, formed as a through hole extending up to the post accommodation 12 according to FIGS. 1, 3, 5a, 5b and 7, whereas the recess 16 according to the second, fourth, sixth and eighth example of FIGS. 2, 4, 6 and 8 is formed as a blind hole.

In the third, fourth, seventh and eighth example according to FIGS. 3, 4, 7 and 8, the recess 16 in a portion close to the endosteal end 14 is conically tapered with a circumferential cutting edge 17 being formed on the endosteal end 14. The external outline of corpus 10 on the endosteal end 14 is conically flared as well.

In the examples five to eight according to FIGS. 5a, 5b, 6, 7 and 8, openings 19 are formed radially to a longitudinal axis 18 of the corpus 10 which are formed as a hollow cylinder shaped hole in these examples. In these examples four openings 19 each are provided in a plane which are arranged in an angle of 90° towards each other. Three of said planes are formed with four openings 19 each distributed over the corpus 10. All these openings 19 either open out into the recess 16 or into the post accommodation 12.

In another example (not shown) the opening can also be lead through the corpus in another location. In still another example the openings are not arranged in one plane but are offset from each other in axial direction.

Figure 9:
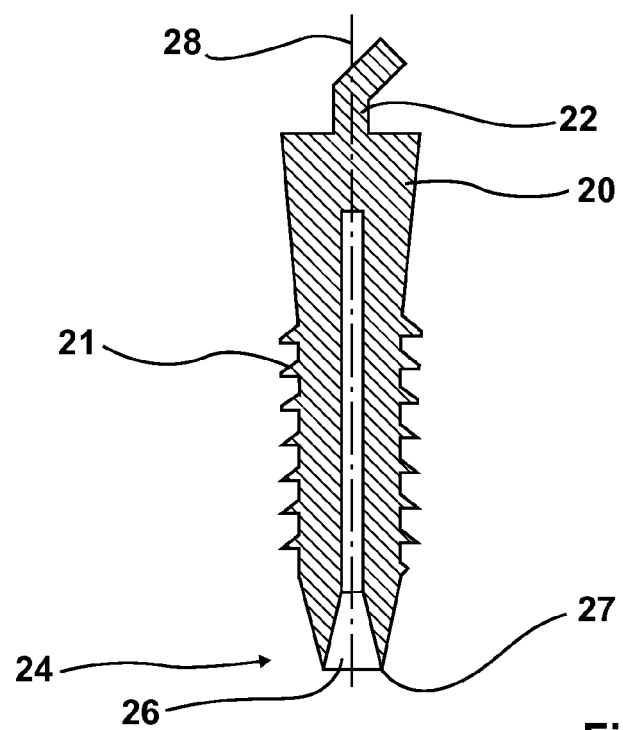
FIG. 9 is a sectional view of a ninth embodiment of a dental implant described herein.
Figure 10:
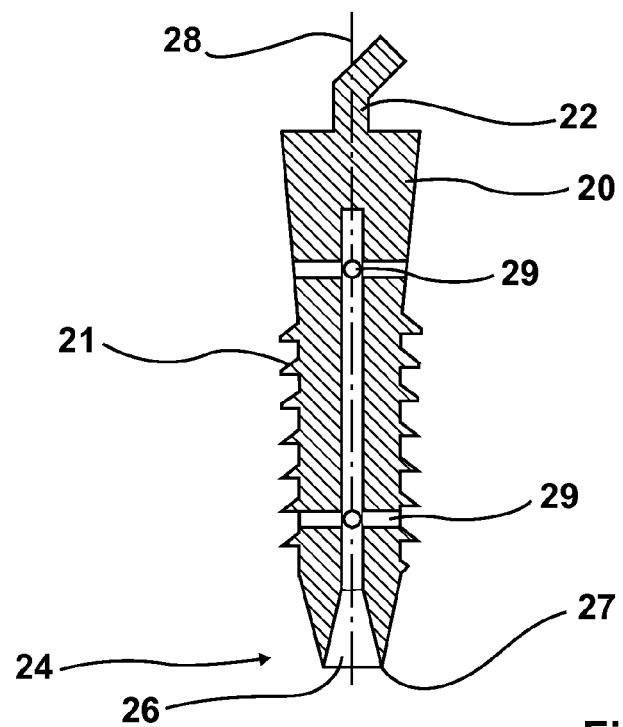
FIG. 10 is a sectional of a tenth embodiment of a dental implant described herein.

In the ninth and tenth example shown in FIGS. 9 and 10, a single-piece dental implant is illustrated likewise having a corpus 20 and an external thread 21. In these two examples, an accommodation 22 is formed to the corpus 20 in one piece onto which the actual dental prosthesis is placed later.

On the endosteal end 24 of the corpus 20 a recess 26 is provided which is formed as a blind hole here with the recess 26 extending close to the coronal end of the corpus 20. On the endosteal end 24 the recess 26 is conically tapered whereas the corpus 20 is conically flared so that a cutting edge 27 is formed on the endosteal end 24.

In the tenth example shown in FIG. 10 openings 29 are provided in addition formed as a through hole extending radially to the longitudinal axis 28 of the corpus 20. On the circumference of the corpus 20 four openings 29 are provided equidistantly so that the individual openings 29 are located rectangular to each other. These openings 29 are located in a common plane with two such planes being provided on the entire corpus 20.

The recesses 16, 26 and the openings 19, 29 cause the surface of the corpus 10, 20 to be increased so that more bone substance can take root on the corpus. Due to this contact surface increased in such a way the grip or hold in the jaw is improved resulting in an improved osseointegration.

Due to the formation of a cutting edge 17, 27 in combination with the recess 16, 26, the dental implant can be inserted into the jaw without pre-drilling. In this process, the cutting edge 17, 27 cuts its way through the jaw with the jaw bone being compressed in this location and received by the recess 16, 26. Due to this compression a certain grip or hold of the dental implant in the corpus occurs already which is even more improved by the increased contact surface. Moreover, the dental implant is maintained well in the jaw also by the external thread 11, 21.

After the dental implant has grown into the jaw, bone substance exists not only in the recess 16, 26 but also in various openings 19, 29 so that the dental implant is downright permeated by bone substance resulting in increased osseointegration.

In view of the foregoing, the examples described herein may provide a dental implant of the type mentioned above, which can well be inserted into the jaw, and which can be anchored permanently in the jaw. The examples of disclosure, as also defined by the claims appended hereto, provide advantageous developed implementations of these dental implants.

The example dental implants configured according to this technical teaching offer the advantage that for the inventive dental implant pre-drilling can be omitted because due to the recess formed on the endosteal end extending coaxially to the longitudinal axis in connection with the conical tapering of the corpus and the cutting edge formed on the endosteal end it is possible to screw said dental implant directly into the jaw. In that case the cutting edge severs the bone at the requested location and the bone thus excised is received by the recess. Due to the conical shaping of the recess, the bone substance is compressed with the result that the dental implant is maintained from the inside by the compressed bone substance and from the outside by the jaw.

In some examples it has provided advantageous that by omitting pre-drilling the entire surgery associated with implanting the dental implant is simplified so that the stress on the patient is reduced as well.

In another example it is possible that the surface of the recess is increased and that the bone substance can even grow into those areas of the post accommodation where there is no post.

In still another example it is possible that bone substance can grow further into the recess formed on the endosteal end on the corpus, and that said bone substance takes root on the surface of the internal recess thus improving osseointegration. This occurs on the one hand due to the fact that lateral stability is increased by the bone substance growing into the recess and on the other hand due to the fact that by the recess the dental implant surface coming into contact with the bone substance is increased so that a larger surface is available for the bone substance to take root.

In yet a further example it is possible that the dental implant surface is increased by the recess so that a larger surface is available for the bone substance to take root. Still another example is that the bone substance need not be removed in the first place, and that the bone substance in the dental implant area compresses itself so that already due to this compression a certain holding pressure is exercised on the dental implant. As a result osseointegration is clearly improved, hence a good and permanent anchoring in the jaw is achieved.

The example dental implants configured according to the second technical teaching offer a multi-piece dental implant is proposed according to the examples with the features of claim 5 and a single-piece dental implant with the features of claim 15. Advantageous further examples of said dental implant are described in the respective dependent claims.

The second example dental implants configured according to this second technical teaching it has provided advantageous that by the opening on the dental implant formed radially to the longitudinal axis of the corpus and penetrating the corpus, a cavity is created into which the bone substance can grow. As has already been explained above, the dental implant surface is increased by this cavity so that more bone substance can take root in order to improve osseointegration.

In some examples, it has proved advantageous that the openings are arranged radially to the longitudinal axis to also prevent the dental implant moving out of the jaw.

In another example the opening is shaped as a hollow cylinder which facilitates placing of the opening on the prepared dental implant which in this case can occur by simple drilling.

Advantageously the opening should not be greater than 1 mm so that dental implant stability is not unduly weakened.

In yet another example the opening is located in the area of the recess and/or in the area of the post accommodation so that bone substance can grow into the recess and into the post accommodation respectively via the opening. This has the advantage that the bone substance can penetrate the dental implant in order to improve osseointegration.

In still a preferred example, two or more openings are arranged in one plane to the longitudinal axis of the corpus, which are advantageously arranged equidistantly. This has the advantage that the bone substance can grow into the dental implant from different sides in order to anchor the dental implant permanently in the jaw.

This application makes reference to, incorporates the same herein by reference, and claims all benefits accruing under 35 U.S.C. §119 from an application for patent filed in the Germany Patent Office on Apr. 8, 2009 and there assigned Serial No. DE 10 2009 016 920.2-43.

Further advantages of the dental implants described herein are apparent. Likewise, the disclosure lies in each and every novel feature or combination of features mentioned above or described herein after. The embodiments discussed herein are merely exemplary and are not intended to limit the scope of the disclosure in any matter. Although, certain example apparatus are described herein, other implementations are possible. The scope of coverage of this patent is not limited to the specific examples described herein. On the contrary, this patent covers all apparatus, methods, and articles of manufacture within the scope if the disclosure.

What is claimed is:

1. A dental implant comprising:
a corpus having a longitudinal axis, a first end, a second end and an external surface having a first diameter and a conical cross-section at the second end;
a post accommodation at the first end, the post accommodation having a first internally threaded portion and a second portion;
a recess having at least a partially conical cross-section and a second diameter at the second end, wherein a width of the conical cross-section of the corpus decreases toward the second end and a width of the conical cross-section of the recess increases toward the second end, wherein the second diameter is substantially equal to the first diameter at the second end to form a tapered cutting edge based on the conical cross-section of the recess and the conical cross-section of the corpus, the cutting edge to cut through a bone;
a first set of openings intersecting the first internally threaded portion of the post accommodation; and
a second set of openings intersecting the second portion of the post accommodation, at least a portion of the first set of openings and at least a portion of the second set of openings to engage the bone when at least a portion of the corpus is disposed in the bone.

2. The dental implant of claim 1, wherein the conical recess is to compress the bone.

3. The dental implant of claim 1, further comprising a third set of openings in the corpus.

4. The dental implant of claim 1, wherein the first set of openings extend transversely to the longitudinal axis.

5. The dental implant of claim 3, wherein the third set of openings intersect at least one of the post accommodation or the recess.

6. The dental implant of claim 3, wherein the third set of openings intersect at least one of the post accommodation or a channel extending coaxial to the longitudinal axis from at least one of the post accommodation or the recess.

7. The dental implant of claim 1, wherein the first set of openings comprises a plurality of openings located at the external surface equidistantly from each other.

8. The dental implant of claim 1, wherein the cutting edge comprises a tapered point at the second end.

9. The dental implant of claim 1, wherein the post accommodation is formed inside the corpus.

10. A dental implant comprising:
a corpus having a longitudinal axis, a first end, a second end and an external surface having a first conical cross-section at the second end;
a post accommodation at the first end, the post accommodation having an internally threaded portion;
a recess having a first portion having a first diameter and a second portion having a second conical cross-section and a second diameter at the second end, the second diameter greater than the first diameter, wherein a width of the second conical cross-section increases toward the second end and a width of the first conical cross-section decreases toward the second end to form a tapered cutting edge;
a first opening intersecting the internally threaded portion of the post accommodation; and
a second opening intersecting the first portion of the recess, at least a portion of the first opening and at least a portion of the second opening to engage a bone when at least a portion of the corpus is disposed in the bone.

11. The dental implant of claim 10, wherein the recess comprises an internal surface and at least a portion of the internal surface is angled at a first angle and at least a portion of the external surface is angled at a second angle such that the internal surface and the external surface meet at the second end.

12. The dental implant of claim 10, where the post accommodation has a non-threaded portion adjacent the threaded portion and further including a second opening intersecting the non-threaded portion.

13. The dental implant of claim 10, wherein the second opening has a third diameter, the first diameter greater than the third diameter.

14. A dental implant comprising:
a corpus having a conical cross-section at an endosteal end of the corpus;
an external thread attached to an endosteal area of the corpus;
a post accommodation formed inside the corpus, the post accommodation having an internally threaded portion;
a recess formed on the endosteal end of the corpus coaxial with a longitudinal axis of the corpus, the recess at least partially conically tapered and having a first diameter at the endosteal end of the corpus, wherein a width of the conical cross-section of the corpus decreases toward the endosteal end and a width of the conical cross-section of the recess increases toward the endosteal end to form a tapered circumferential cutting edge adjacent to the recess at the endosteal end of the corpus;
a channel extending coaxial to the longitudinal axis of the corpus from at least one of the post accommodation or the recess, the channel having a second diameter, the first diameter greater than the second diameter; and
a first opening intersecting the internally threaded portion of the post accommodation, at least a portion of the opening to engage a bone when at least a portion of the corpus is disposed in the bone.

15. The dental implant of claim 14, wherein the first opening is formed radially to the longitudinal axis of the corpus.

16. The dental implant of claim 15, wherein the first opening is at least partially a hollow cylinder.

17. The dental implant of claim 16, wherein the first opening has an inner diameter of not more than about 1 mm.

18. The dental implant of claim 14, further comprising a second opening coupled to the recess.

19. The dental implant of claim 14, further comprising a second opening coupled to the post accommodation.

20. The dental implant of claim 14, further comprising a second opening, wherein the first opening and the second opening are transverse to the longitudinal axis of the corpus.

21. The dental implant of claim 20, wherein the first opening and the second opening are equidistant to the longitudinal axis of the corpus.

22. The dental implant of claim 21, wherein the circumferential cutting edge comprises a pointed edge at the endosteal end of the corpus, the pointed edge to cut bone.

* * * * *